US010330685B2

(12) United States Patent
Stringer et al.

(10) Patent No.: US 10,330,685 B2
(45) Date of Patent: Jun. 25, 2019

(54) MARKERS FOR SEPSIS TREATMENT

(71) Applicants: THE REGENTS OF THE UNIVERSITY OF MICHIGAN, Ann Arbor, MI (US); UNIVERSITY OF MISSISSIPPI MEDICAL CENTER, Jackson, MS (US)

(72) Inventors: Kathleen Stringer, Ann Arbor, MI (US); Alan E. Jones, Jackson, MS (US); Mike Puskarich, Madison, MS (US)

(73) Assignees: THE REGENTS OF THE UNIVERSITY OF MICHIGAN, Ann Arbor, MI (US); UNIVERSITY OF MISSISSIPPI MEDICAL CENTER, Jackson, MS (US)

( * ) Notice: Subject to any disclaimer, the term of this patent is extended or adjusted under 35 U.S.C. 154(b) by 88 days.

(21) Appl. No.: 15/307,920

(22) PCT Filed: Apr. 28, 2015

(86) PCT No.: PCT/US2015/027956
§ 371 (c)(1),
(2) Date: Oct. 31, 2016

(87) PCT Pub. No.: WO2015/168100
PCT Pub. Date: Nov. 5, 2015

(65) Prior Publication Data
US 2017/0052192 A1    Feb. 23, 2017

Related U.S. Application Data

(60) Provisional application No. 61/987,319, filed on May 1, 2014.

(51) Int. Cl.
| | | |
|---|---|---|
| *A61K 9/00* | (2006.01) | |
| *A61K 45/06* | (2006.01) | |
| *G01N 33/64* | (2006.01) | |
| *A61K 38/48* | (2006.01) | |
| *A61K 31/205* | (2006.01) | |

(52) U.S. Cl.
CPC ........... *G01N 33/64* (2013.01); *A61K 9/0019* (2013.01); *A61K 9/0053* (2013.01); *A61K 31/205* (2013.01); *A61K 38/4866* (2013.01); *A61K 45/06* (2013.01); *C12Y 304/21069* (2013.01); *G01N 2800/26* (2013.01); *G01N 2800/52* (2013.01)

(58) Field of Classification Search
None
See application file for complete search history.

(56) References Cited

U.S. PATENT DOCUMENTS

| | | |
|---|---|---|
| 5,814,661 A | 9/1998 | Ruggiero et al. |
| 2009/0104596 A1 | 4/2009 | Assadi Porter et al. |
| 2012/0202240 A1 | 8/2012 | Deigner et al. |
| 2013/0071866 A1 | 3/2013 | Kido et al. |
| 2014/0107201 A1 | 4/2014 | Williams et al. |

FOREIGN PATENT DOCUMENTS

| | | |
|---|---|---|
| EP | 0566971 A1 | 10/1993 |
| WO | 2015168100 A1 | 11/2015 |

OTHER PUBLICATIONS

Hatannkhani, Carnitine and Sepsis: A Review of an Old Clinical Dilemma, J Pharm Pharm Sci., 16(3) 414-423, 2013.*
Eaton et al., "Myocardial carnitine palmitoyltransferase I as a target for oxidative modification in inflammation and sepsis." Biochem Soc Trans. Dec. 2003;31(Pt 6):1133-6.
Fink "Bench-to-bedside review: Cytopathic hypoxia." Crit Care. Dec. 2002;6(6):491-9.
Gasparetto et al., "Influence of acetyl-L-carnitine infusion on haemodynamic parameters and survival of circulatory-shock patients." Int J Clin Pharmacol Res. 1991;11(2):83-92.
Nanni et al., "Plasma camitine levels and urinary carnitine excretion during sepsis." Parenter Enteral Nutr. Jul.-Aug. 1985;9(4):483-90.
Puskarich et al., "Preliminary safety and efficacy of L-carnitine infusion for the treatment of vasopressor-dependent septic shock: a randomized control trial." J Parenter Enteral Nutr. Aug. 2014;38(6):736-43.
Sawhney et al., "Bioerodible Hydrogels Based on Photopolymerized Poly(ethyleneglycol)-co-poly(a-hydroxy acid) Diacrylate Macromers" Macromolecules, 1993, 26 (4), pp. 581-587.
Vary "Sepsis-induced alterations in pyruvate dehydrogenase complex activity in rat skeletal muscle: effects on plasma lactate." Shock. Aug. 1996;6(2):89-94.
Comprehensive Heterocyclic Chemistry II, A. R. Katritzky and C. W. Rees (Eds) Pergamon, Oxford 1996, vol. 1-11. Table of Contents provided, sections available upon Examiner request.
Comprehensive Heterocyclic Chemistry, A. R. Katritzky and C. W. Rees (Eds) Pergamon, Oxford 1984, vol. 1-9. Sections available upon Examiner request.
Comprehensive Organic Synthesis, B. Trost and I. Fleming (Eds.) vol. 1-9 Pergamon, Oxford, 1991. Sections available upon Examiner request.
Fieser and Fieser's Reagents for Organic Synthesis, Wiley & Sons: New York, vols. 1-21. Sections available upon Examiner request.
Organic Reactions, Wiley & Sons: New York, 1991, vols. 1-40. Sections available upon Examiner request.
R. C. LaRock, Comprehensive Organic Transformations, 2nd edition Wiley-VCH, New York 1999. Sections available upon Examiner request.
Remington's Pharmaceutical Sciences, 18th edition, edited by A. R. Gennaro, Mack Publishing Co., 1990. Sections available upon Examiner request.

(Continued)

*Primary Examiner* — Louise W Humphrey
*Assistant Examiner* — Srikanth Patury
(74) *Attorney, Agent, or Firm* — Casimir Jones, S.C.

(57) ABSTRACT

Provided herein is technology relating to treatment of sepsis and particularly, but not exclusively, to methods for predicting a response of a sepsis patient to treatment with L-carnitine.

8 Claims, 11 Drawing Sheets

(56) References Cited

OTHER PUBLICATIONS

Remingtons Pharmaceutical Sciences, Mack Publishing Co. (A. R. Gennaro edit. 1985. sections available upon Examiner request.
Stringer KA et al. "L-Carnitine Treatment Impacts Amino Acid and Energy Metabolism in Sepsis As Detected by Untargeted 1H-Nuclear Magnetic Resonance (NMR) Pharmacometabolomics"; meeting abstract A3932 for American Thoracic Society 2014 International Conference (May 20, 2014; San Diego, California) published in Am J Respir Crit Care Med 189: A3932 (2014).
International Search Report of related PCT/US2015/027956, dated Jul. 28, 2015, 11 pages.

\* cited by examiner

MARKERS FOR SEPSIS TREATMENT

This application is a § 371 U.S. National Phase Entry of pending International Application Number PCT/US2015/027956, filed Apr. 28, 2015, which claims priority to U.S. provisional patent application Ser. No. 61/987,319, filed May 1, 2014, each of which is incorporated herein by reference in its entirety.

FIELD

Provided herein is technology relating to treatment of sepsis and particularly, but not exclusively, to methods for predicting a response of a sepsis patient to treatment with L-carnitine.

BACKGROUND

Sepsis affects more than 750,000 patients annually in the United States and has a mortality rate of from 30 to 65%, which makes it the tenth most common cause of death in the U.S. The risk of sepsis is found to be inversely related to age. Sepsis accounts for 60 to 80% of childhood deaths in the developing world. As a result of its prevalence, hospital visits for sepsis or septicemia increased from 621,000 in the year 2000 to 1,141,000 in 2008. In economic terms, total costs for treating sepsis increased by an average of 11.9% each year between 1997 and 2008, adjusted for inflation, and amounted to $14.6 billion in the U.S. in 2008 and currently exceed $17 billion. In addition to other hospital treatments, over 2.5 million patients are admitted annually to ICUs for sepsis with the costs per individual ICU case adding $5,000 or more per day to total hospital costs and with treatment lasting at least two days and often more than 20 days. Additionally, nearly 50 percent of diagnosed sepsis cases in the U.S. are attributable to hospital-acquired infections (HAIs), which impose a major direct cost on hospitals due to little to no reimbursement from health insurers.

Sepsis is the body's response to infection. This response is characterized by the cardinal signs of inflammation (e.g., vasodilation, leukocyte accumulation, and increased microvascular permeability) occurring in tissues that are remote from the infection. Even a minor infection, such as strep throat or influenza, can trigger sepsis. Sepsis is usually not life-threatening, but complications of sepsis can cause serious illness and death.

Sepsis is a general term describing immune responses within a continuum from infection to multiple organ dysfunction syndrome. Systemic inflammatory response syndrome (SIRS) is the presence of two or more of abnormal body temperature, heart rate, respiratory rate or blood gas, and white blood cell count, and sepsis is defined as SIRS in response to an infectious process. Severe sepsis is defined as sepsis with sepsis-induced organ dysfunction or tissue hypoperfusion (e.g., manifesting as hypotension, elevated lactate, or decreased urine output). Severe sepsis occurs when a natural immune response to an infection triggers widespread inflammation and blood clotting in tiny vessels throughout the body, which also involves failure of critical organs in the body and can thus lead to death. Finally, septic shock is severe sepsis plus persistently low blood pressure.

Currently, measures for diagnosing sepsis and estimating its severity, prognosis, and the efficacy of therapy include laboratory tests that monitor the evidence of infection; clotting problems; liver or kidney function; oxygen availability; electrolyte levels; and/or cardiovascular, neurologic, or hematologic function. Often these parameters are used to derive illness severity and/or prognosis scores like the Sequential Organ Failure Assessment (SOFA) score. If the site of the infection is not obvious, imaging tests such as X-ray, computerized tomography (CT), ultrasound, or, less commonly, magnetic resonance imaging (MRI), are often performed.

While the existing technologies for treating sepsis have increased success rates of therapies, the management of sepsis remains complicated by inherent difficulties in diagnosis, delayed recognition of organ dysfunction, and a poorly characterized biological phenotype. As such, patient outcomes are compromised and the development of therapies to achieve optimal outcomes (e.g., reduce mortality) are hampered. In addition, use of existing technologies has been limited by an inability to select patients who will most likely benefit from specific treatments and to titrate dosing and duration appropriately.

Some previous approaches have attempted to address this problem using pharmacogenomics to predict drug response in sepsis patients. However, this approach has had limited success due to inconsistencies and limited understanding of the biological indications predictive of successful treatment. Thus, there is a growing need for biomarkers that can indicate both the responsiveness of a patient to a drug and how to titrate the dosage appropriately for a patient.

SUMMARY

Data suggest that certain metabolic disturbances associated with sepsis are associated with poor medical outcomes. In particular, deficiency in L-carnitine, which is a branched non-essential amino acid, may contribute to metabolic dysfunctions involved in certain aspects of sepsis. As a result, clinical trials are underway to evaluate the efficacy of L-carnitine in the treatment of sepsis and, in particular, to ameliorate vasopressor-dependent septic shock (see, e.g., Puskarich et al. J Parenter Enteral Nutr 38(6): 736-743, incorporated herein by reference in its entirety).

The technology described herein provides a "pharmacometabolomics" strategy for personalized medicine as exemplified by embodiments of the technology applied to the treatment of sepsis. In particular, some embodiments provide technology related to the use of metabolite levels (e.g., amounts, concentrations, masses, etc.) measured in a patient sample (e.g., blood, e.g., serum) to identify sepsis patients who are most likely to respond to treatment with L-carnitine. Specifically, data collected during the development of the technology provided herein indicate that certain metabolites differentiate patients as either "carnitine responders" or "carnitine non-responders", thus providing for an individualized and targeted carnitine therapy for identified groups of septic patients.

Experiments conducted during the development of the technology provided herein included metabolomics assays performed with serum samples acquired as part of a preliminary safety and efficacy study of L-carnitine. As a result, data were collected that identified exemplary blood (e.g., serum) metabolites (e.g., small molecules) that are predictive of a sepsis patient's response to treatment with L-carnitine. For example, the technology comprises embodiments related to assessing biomarkers including, but not limited to, ketone bodies, acetylcarnitine (AC), carnitine (C), and the AC:C ratio. Data acquired by $^1$H-nuclear magnetic resonance (NMR) showed that the pre-treatment levels of ketone bodies (e.g., 3-hydroxybutyrate and acetoacetate) and the acetylcarnitine:carnitine ratio differentiate L-carnitine responders from non-responders. For example, patients having "low" amounts of ketone prior to treatment with L-carnitine had significantly better survival than patients with "high" amounts of ketone prior to L-carnitine treatment (see below for definition of "low" and "high" amounts). Additionally, data were collected identifying certain metabolites of the L-carnitine drug response that change over time with L-carnitine treatment. Particular markers included amino acids such as methionine, lysine, phenylalanine, tyrosine, ornithine, serine, threonine, and valine. Such markers find use in monitoring the effectiveness of a drug (e.g., L-carnitine) and the occurrence of potential adverse drug reactions.

Thus, particular embodiments of the technology provide novel predictive and pharmacodynamic serum biomarkers for treatment of sepsis patients with L-carnitine. Clinical data have indicated that traditional phenotyping (e.g., based on a SOFA score) alone cannot differentiate sepsis patients into groups predicted to respond and not to respond to treatment. In contrast, the metabolic data collected during the development of the technology described herein identifies patients who are likely to respond to therapy. Consequently, the technology provided herein provides important information to medical and clinical practitioners for making therapeutic decisions early in the course of this severe illness.

This technology provides a novel and generally applicable "pharmacometabolomics" strategy for personalized medicine. Data collected during the development of the technology indicate that it provides a sensitive and quantitative approach to predict drug responses (e.g., positive responses and adverse drug reactions), e.g., for the diagnosis and treatment of sepsis. It is contemplated that the technology finds use in point-of-care diagnostics for the treatment of sepsis patients with L-carnitine.

Advantages of the technology include the ability to identify responders to L-carnitine therapy for sepsis, thus enabling clinical therapeutic decision-making early in the course of the disease. In addition, sample collection associated with the technology is minimally invasive—blood serum-based tests are well-accepted by patients and are widely used in clinical settings. Consequently, the tests can be prescribed routinely and frequently as a precautious measure to monitor high risk patient populations.

Accordingly, provided herein is technology related to a method for treating a subject having sepsis, the method comprising measuring one or more of a level of acetoacetate, a level of 3-hydroxybutyrate, a level of carnitine, a level of acetylcarnitine and/or a level of creatine in a sample (e.g., a blood sample (e.g., a serum sample)) and/or calculating a ratio of acetylcarnitine (AC) level to carnitine (C) level based on measurements of acetylcarnitine and carnitine from a subject sample; identifying the subject as a carnitine responsive subject if the acetoacetate level is less than or equal to 25 μM, the 3-hydroxybutyrate level is less than or equal to 150 μM, the creatine level is less than or equal to 30 μM, and/or the AC:C ratio is less than or equal to 0.4; and administering carnitine to a carnitine responsive subject. The carnitine is administered by one of many appropriate routes known in the art. For example, in some embodiments the carnitine is administered intravenously (e.g., 1 g to 20 g of the carnitine is administered over 1 to 24 hours) and in some embodiments the carnitine is administered orally (e.g., carnitine is provided in a dose of approximately 1 g to 3 g per dose).

The levels of ketone bodies are associated with a subject's response to carnitine therapy. For example, in some embodiments the methods comprise predicting a carnitine responsive subject to have a serum concentration of carnitine that is less than 200 μM at a time that is approximately 24 hours after the administration of carnitine, predicting a carnitine responsive subject to have a serum concentration of O-acetyl-carnitine that is less than 50 μM at a time that is approximately 24 hours after the administration of carnitine, predicting a carnitine responsive subject compared with a carnitine non-responsive subject also to have a serum concentration of lysine that is greater than 100 μM at a time that is approximately 24 hours after the administration of carnitine, and/or predicting a carnitine responsive subject to have a serum concentration of methionine that is greater than 25 μM at a time that is approximately 24 hours after the administration of carnitine. In some embodiments, the technology comprises predicting a carnitine responsive subject as having a lower level of one or more of carnitine or O-acetyl-carnitine, with associated increasingly higher levels of methionine, lysine, phenylalanine, tyrosine, ornithine, serine, threonine, valine, acetoacetate, 3-hydroxybutyrate, and/or citrate at a time that is approximately 24 hours after the administration of carnitine, (e.g., an increased level is present at 20 to 50 hours after administration of carnitine). In some embodiments, administration of carnitine ameliorates a metabolic abnormality in the subject.

The technology also provides biomarkers associated with carnitine treatment that are useful for monitoring treatment and/or the presence of adverse reactions. Accordingly, some embodiments comprise monitoring a concentration of one or more biomarkers selected from the group consisting of carnitine, O-acetyl-carnitine, methionine, lysine, phenylalanine, tyrosine, ornithine, serine, threonine, valine, ketone bodies (e.g., acetoacetate and/or 3-hydroxybutyrate), and citrate in a subject sample; and/or calculating and monitoring the AC:C ratio at a time that is from 20 to 100 hours after the administration of carnitine. Some embodiments provide for identifying the subject as responding to carnitine treatment if an increase in the concentration of the one or more biomarkers is detected in the sample.

In a related aspect, the technology provides a method of treating a subject for a carnitine deficiency, the method comprising measuring the plasma concentrations of a ketone body, carnitine, and/or acylcarnitine; and administering carnitine to the subject if the acylcarnitine to carnitine ratio is greater than 0.4 or the carnitine concentration is less than 20 μmol/liter. In some embodiments, the methods comprise administering carnitine to the subject if the ketone body is acetoacetate and the acetoacetate level is less than or equal to 25 μM or if the ketone body is 3-hydroxybutyrate and the 3-hydroxybutyrate level is less than or equal to 150 μM.

The technology finds use in treating sepsis and related conditions, e.g., in some embodiments the subject has systemic inflammatory response syndrome, sepsis, severe sepsis, or septic shock. The technology also finds use in general treatment of a metabolic deficiency.

For instance, provided herein are embodiments of a method of treating a subject having sepsis, the method comprising administering carnitine to the subject. In some embodiments, a subject is identified as having sepsis by measuring a biomarker that is carnitine, acetylcarnitine, or a ketone body; and detecting a symptom that is abnormal body temperature, heart rate, respiratory rate, blood gas, or white blood cell count; hypotension; elevated lactate; decreased urine output; inflammation; blood clotting; or persistently low blood pressure. Further, in some embodiments the methods comprise measuring a biomarker of sepsis that is procalcitonin, C-reactive protein, and/or heparin binding protein and, in some embodiments, the methods comprise administering activated protein C or an antibiotic to the subject, e.g., simultaneous with the administration of carnitine, before the administration of carnitine, or after the administration of carnitine.

In some embodiments, the technology relates to embodiments of kits comprising, consisting of, or consisting essentially of, reagents for detecting, quantifying, assaying, measuring, etc. one or more biomarkers. For example, in some embodiments the technology provides a kit comprising one or more detection reagents to measure the amount, concentration, mass, etc. of a ketone body (e.g., acetoacetate and/or 3-hydroxybutyrate) in a sample from a subject (e.g., a blood, plasma, or serum sample) and/or one or more additional biomarkers as described herein (e.g., carnitine, acetylcarnitine; an amino acid such as methionine, lysine, phenylalanine, tyrosine, ornithine, serine, threonine, and/or valine; and/or citrate). In some embodiments, kits comprise one or more detection reagents specific for a ketone body, carnitine, and/or acylcarnitine, and one or more detection reagents for a biomarker that is procalcitonin (PCT), C-reactive protein (CRP), and/or heparin binding protein (HBP). In some embodiments of kits, the kit comprises a reagent for measuring a symptom of a subject such as abnormal body temperature, heart rate, respiratory rate, blood gas, or white blood cell count; hypotension; elevated lactate; decreased urine output, inflammation, blood clotting, or persistently low blood pressure. In some embodiments of kits, vessels are provided for taking a sample from a patient (e.g., a syringe or other device for acquiring a blood sample from a subject). In some embodiments of kits, the kits comprise one or more unit doses of carnitine for administration to a subject in a dosage based on the result of detecting one or more biomarkers using the detection reagents of the kit.

In some embodiments, the technology provides automated methods for processing data comprising an amount of a biomarker measured in a patient sample and returning a report to a user comprising an indication that the patient has sepsis and/or a dosage of carnitine to administer to the patient. For example, embodiments provide a method for reporting a carnitine dosage, the method comprising obtaining a carnitine level measured in a patient sample; obtaining an acylcarnitine level measured in the patient sample; calculating a ratio of the acylcarnitine level to the carnitine level; and providing a report comprising a carnitine dosage. The measured levels may be obtained by a doctor or clinical personnel for input into a computer or the measured levels may be obtained by a remote laboratory from medical personnel and the result returned to the medical personnel. In particular, methods are related to providing a report that comprises an instruction to administer a carnitine dosage when the acylcarnitine to carnitine ratio is greater than 0.4. Additional embodiments provide a method comprising obtaining the measured level(s) of one or more biomarker(s) that is/are: acetoacetate and/or 3-hydroxybutyrate; methionine, lysine, phenylalanine, tyrosine, ornithine, serine, threonine, and/or valine; citrate; and/or procalcitonin (PCT), C-reactive protein (CRP), and/or heparin binding protein (HBP); and reporting the level(s) of the one or more biomarkers. Specific embodiments comprise providing an instruction to administer carnitine if the acetoacetate level is less than or equal to 25 µM or the 3-hydroxybutyrate level is less than or equal to 150 µM and/or identifying the patient as having sepsis based on the amount of procalcitonin (PCT), C-reactive protein (CRP), and/or heparin binding protein (HBP) in the patient sample.

In addition, the technology provides embodiments of systems for determining a course of treatment, the system comprising one or more detection reagents for determining one or more sepsis biomarkers and/or one or more ketone biomarkers; and a computer configured to perform a method as described herein. Some system embodiments provide the detection reagent in a kit as described herein, e.g., comprising one or more detection reagents for assaying one or more ketone biomarkers and one or more sepsis biomarkers.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings, which represent the analysis of patients enrolled in a phase I study of L-carnitine in septic shock (see, e.g., Puskarich et al. J Parenter Enteral Nutr 38(6): 736-743, incorporated herein by reference in its entirety). From this study, serum samples collected from carnitine-treated (n=16) and placebo-treated (n=14) patients were assayed by $^1$H-nuclear magnetic resonance (NMR) and the resulting spectra were used to identify and quantify metabolites; a total of 38 metabolites were identified in each sample.

Figure 1:
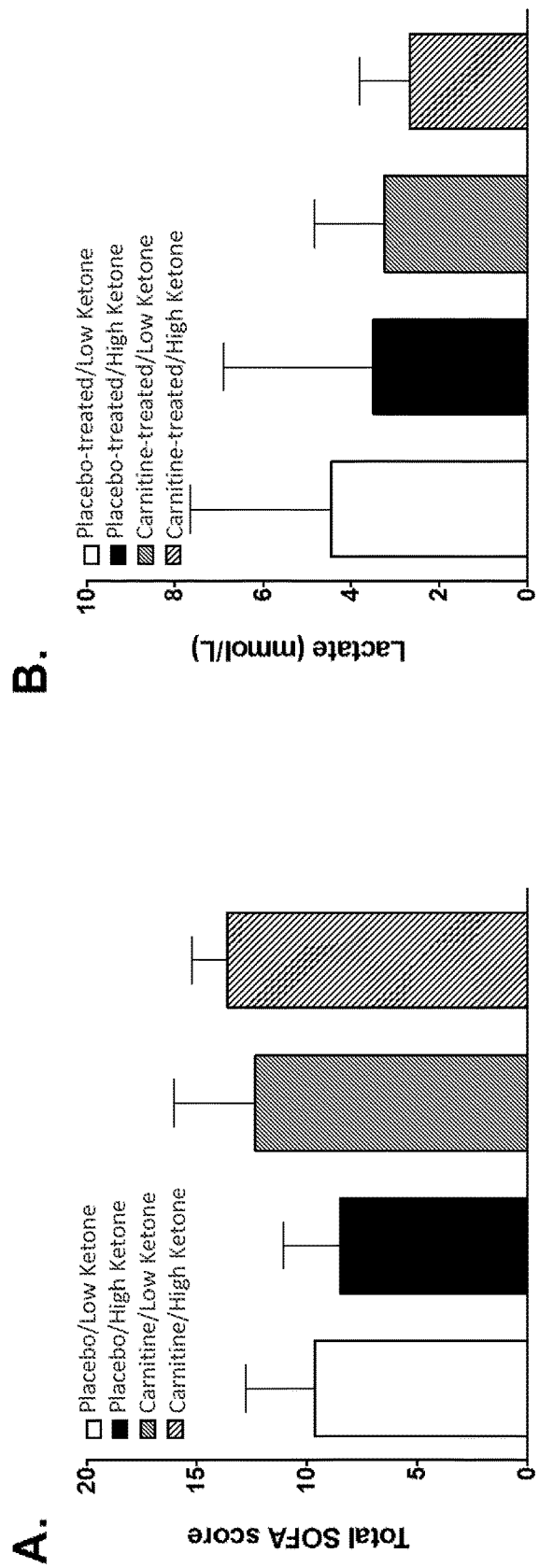
FIG. 1 shows bar plots of the median (+ range) (A) SOFA scores and concentrations of (B) lactate, (C) glucose, (D) acetylcarnitine:carnitine ratio, (E) 3-hydroxybutyrate, and (F) acetoacetate in advance (pre-treatment, time 0) of randomization to either carnitine treatment or placebo. Pre-treatment creatine was also higher in "high" ketone patients that were randomized to carnitine compared with the other groups. Measured and calculated values are shown for low and high ketone groups treated with carnitine or placebo.
Figure 1:
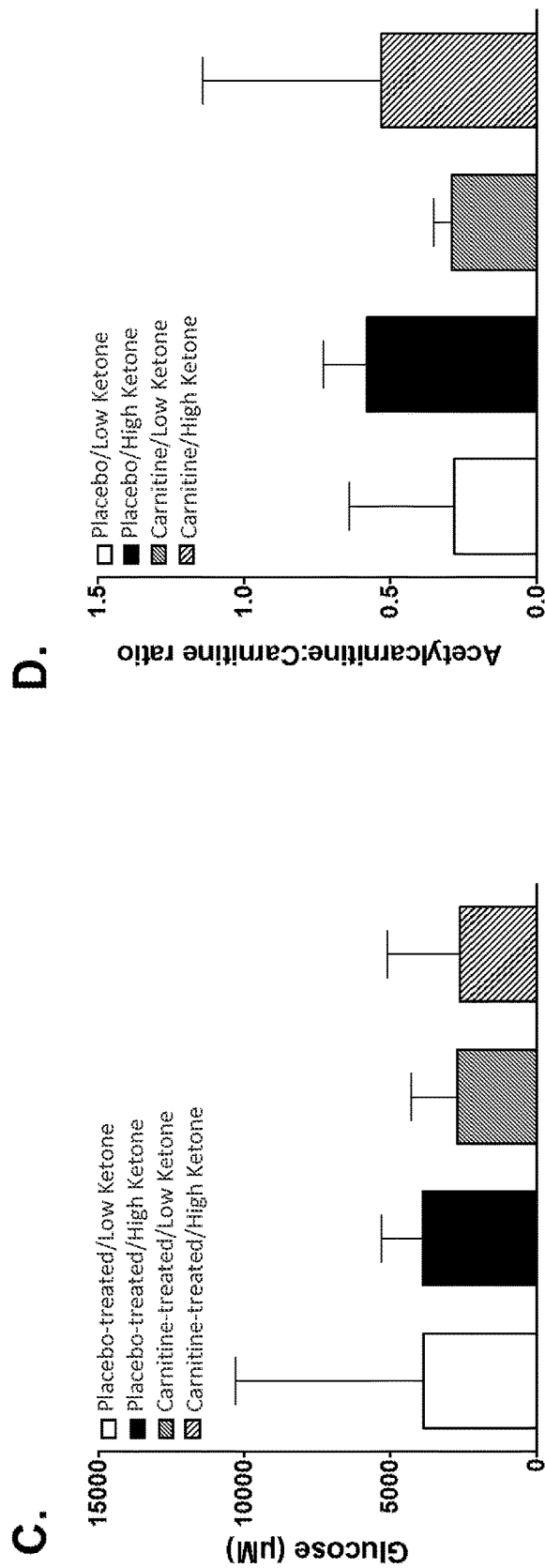
Figure 1:
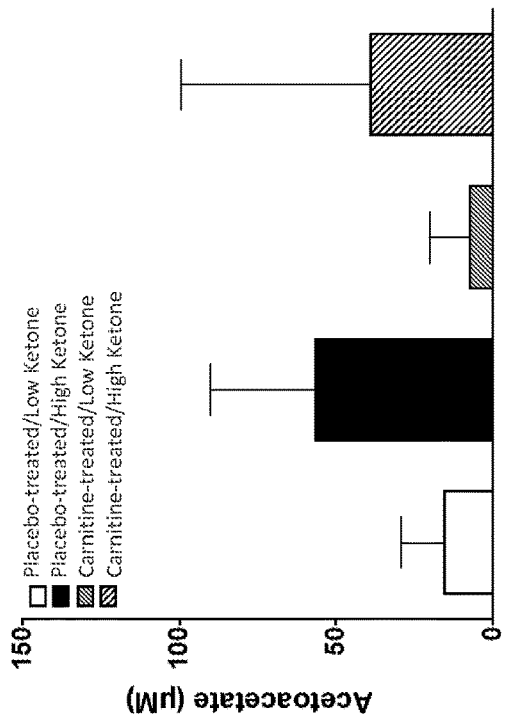
Figure 1:
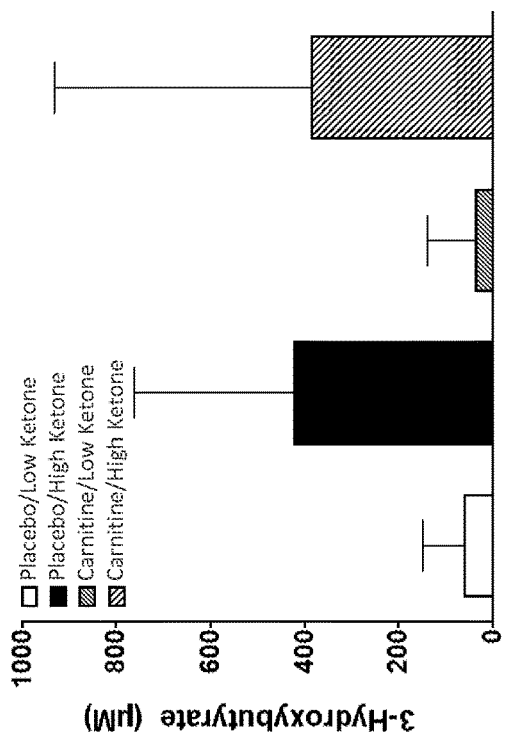

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

The technology provided herein relates to methods for predicting the response to and monitoring the response of a subject having sepsis after treatment with carnitine (e.g., L-carnitine). In one aspect, embodiments of the technology relate to measuring the concentrations of certain metabolites that predict the metabolic response and outcomes (e.g., mortality) to carnitine treatment. Some embodiments relate to measuring metabolite levels to differentiate subjects that are more likely to respond to treatment with carnitine from those subjects who are less likely to respond to treatment with carnitine. Moreover, the technology relates to certain metabolites whose concentrations change after treatment with carnitine, thus providing methods to monitor treatment and to evaluate the risk of adverse outcomes of treatment.

Aspects of the technology are described below. In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein. The section headings used herein are for organizational purposes only and are not to be construed as limiting the described subject matter in any way.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the term "treatment" is defined as the application or administration of a therapeutic agent described herein (e.g., carnitine) to a patient, or application or administration of the therapeutic agent to an isolated tissue or cell line from a patient, who has a disease (e.g., sepsis), a symptom of disease or a predisposition toward a disease, with the purpose to cure, heal, alleviate, relieve, alter, remedy, ameliorate, improve or affect the disease, the symptoms of disease, or the predisposition toward disease.

Compositions according to the technology can be administered in the form of pharmaceutically acceptable salts. The term "pharmaceutically acceptable salt" refers to a salt that possesses the effectiveness of the parent compound and is not biologically or otherwise undesirable (e.g., is neither toxic nor otherwise deleterious to the recipient thereof). Suitable salts include acid addition salts that may, for example, be formed by mixing a solution of the compound of the present technology with a solution of a pharmaceutically acceptable acid such as hydrochloric acid, sulfuric acid, acetic acid, trifluoroacetic acid, or benzoic acid. Certain of the compounds employed in the present technology may carry an acidic moiety (e.g., COOH or a phenolic group), in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (COOH) or alcohol group being present, pharmaceutically acceptable esters can be employed to modify the solubility or hydrolysis characteristics of the compound.

The term "administration" and variants thereof (e.g., "administering" a compound) in reference to a compound mean providing the compound or a prodrug of the compound to the individual in need of treatment or prophylaxis. When a compound of the technology or a prodrug thereof is provided in combination with one or more other active agents, "administration" and its variants are each understood to include provision of the compound or prodrug and other agents at the same time or at different times. When the agents of a combination are administered at the same time, they can be administered together in a single composition or they can be administered separately. As used herein, the term "composition" is intended to encompass a product comprising the specified ingredients in the specified amounts, as well as any product that results, directly or indirectly, from combining the specified ingredients in the specified amounts.

By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation, or experiment.

The term "effective amount" as used herein means that amount of active compound or pharmaceutical agent (e.g., carnitine) that elicits the biological or medicinal response in a cell, tissue, organ, system, animal, or human that is being sought by a researcher, veterinarian, medical doctor, or other clinician. In some embodiments, the effective amount is a "therapeutically effective amount" for the alleviation of the symptoms of the disease or condition being treated. In some embodiments, the effective amount is a "prophylactically effective amount" for prophylaxis of the symptoms of the disease or condition being prevented. The term also includes herein the amount of active compound sufficient to treat sepsis and thereby elicit a response being sought. When the active compound is administered as the salt, references to the amount of active ingredient are to the free form (the non-salt form) of the compound. In some embodiments, the dosage of the compound or related compounds will generally range from 0.001 to 10,000 mg/kg/day or dose (e.g., 0.01 to 1000 mg/kg/day or dose; 0.1 to 100 mg/kg/day or dose).

In the method of the present technology, compounds, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the technology can, for example, be administered orally, parenterally (including subcutaneous injections, intravenous, intramuscular, intrasternal injection, or infusion techniques), by inhalation spray, or rectally, in the form of a unit dosage of a pharmaceutical composition containing an effective amount of the compound and conventional non-toxic pharmaceutically-acceptable carriers, adjuvants, and vehicles. Liquid preparations suitable for oral administration (e.g., suspensions, syrups, elixirs, and the like) can be prepared according to techniques known in the art and can employ any of the usual media such as water, glycols, oils, alcohols, and the like. Solid preparations suitable for oral administration (e.g., powders, pills, capsules, and tablets) can be prepared according to techniques known in the art and can employ such solid excipients as starches, sugars, kaolin, lubricants, binders, disintegrating agents, and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution, or a solution containing a mixture of saline and glucose. Further description of methods suitable for use in preparing pharmaceutical compositions for use in the present technology and of ingredients suitable for use in said compositions is provided in *Remington's Pharmaceutical Sciences,* 18th edition, edited by A. R. Gennaro, Mack Publishing Co., 1990. Compounds of the present technology can be made by a variety of methods depicted in the synthetic reaction schemes provided herein. The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis,* Wiley & Sons: New York, Volumes 1-21; R. C. LaRock, *Comprehensive Organic Transformations,* 2nd edition Wiley-VCH, New York 1999; *Comprehensive Organic Synthesis,* B. Trost and I. Fleming (Eds.) vol. 1-9 Pergamon, Oxford, 1991; *Comprehensive Heterocyclic Chemistry,* A. R. Katritzky and C. W. Rees (Eds) Pergamon, Oxford 1984, vol. 1-9; *Comprehensive Heterocyclic Chemistry II,* A. R. Katritzky and C. W. Rees (Eds) Pergamon, Oxford 1996, vol. 1-11; and *Organic Reactions,* Wiley & Sons: New York, 1991, Volumes 1-40.

Description

Provided herein is technology relating to treatment of sepsis and particularly, but not exclusively, to methods for predicting a response of a sepsis patient to treatment with L-carnitine. The technology relates to methods for differentiating (e.g., metabolic phenotyping) patients (e.g., sepsis patients) who are likely to respond favorably to treatment with carnitine. In addition, the technology provides methods for predicting the changes in a sepsis patient's metabolism (e.g., changes in the concentrations of particular metabolites) after treatment with carnitine. Although the disclosure herein refers to certain illustrated embodiments, it is to be understood that these embodiments are presented by way of example and not by way of limitation.

Treatment of Sepsis with L-Carnitine

Carnitine (e.g., L-carnitine or levocarnitine) is a substance required in mammalian energy metabolism. It has been shown to facilitate long-chain fatty acid entry into cellular mitochondria, thereby delivering substrate for oxidation and subsequent energy production. Fatty acids are utilized as an energy substrate in all tissues except the brain. In skeletal and cardiac muscle, fatty acids are the main substrate for energy production. Primary systemic carnitine deficiency is characterized by low concentrations of carnitine in plasma, red blood cells, and/or tissues.

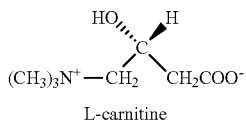

L-carnitine

Evidence suggests the presence of mitochondrial dysfunction during sepsis and that this dysfunction is associated with adverse clinical outcomes (see Fink (2002) "Bench-to-bedside review: cytopathic hypoxia" Crit Care. 6: 491-499). Among the mitochondrial alterations reported in sepsis are inhibition of pyruvate dehydrogenase (PDH) and carnitine palmitoyl transferase 1 (CPT-1)) (Eaton et al (2003) "Myocardial carnitine palmitoyltransferase 1 as a target for oxidative modification in inflammation and sepsis" Biochem Soc Trans. 31: 1133-1136; Vary (1996) "Sepsis-induced alterations in pyruvate dehydrogenase complex activity in rat skeletal muscle: effects on plasma lactate" Shock 6: 89-94.) Specifically, with regard to CPT-1, a systemic carnitine deficiency results from increased urinary secretion of carnitine (Nani et el (1985) "Plasma carnitine levels and urinary carnitine excretion during sepsis" JPEN J Parenter Enteral Nutr. 9: 483-490). Animal models of sepsis demonstrate favorable effects of carnitine on mortality, and human studies of L-carnitine for septic shock demonstrated improvements in hemodynamic parameters, including right atrial pressure, mean arterial pressure, and arterial oxygenation (Gasparetto et al (1991) "Influence of acetyl-L-carnitine infusion on haemodynamic parameters and survival of circulatoryshock patients" Int J Clin Pharm Res. 11: 83-92).

Carnitine deficiency is defined biochemically as abnormally low plasma concentrations of free carnitine, e.g., less than 20 µmol/liter, and may be associated with low tissue and/or urine concentrations. Further, this condition may be associated with a plasma concentration ratio of acylcarnitine/carnitine greater than 0.4 or abnormally elevated concentrations of acylcarnitine in the urine.

Subjects

In some embodiments, the technology is related to administering carnitine to a subject in need of a treatment for sepsis. In some embodiments, the subject is in need of treatment for sepsis and does not have a metabolic disorder, an inborn error of metabolism, or end stage renal disease; in some embodiments, the subject is in need of treatment for sepsis and has a metabolic disorder, an inborn error of metabolism, or end stage renal disease. In some embodiments, the subject is in need of treatment for sepsis and has not been nor is being treated for a metabolic disorder, an inborn error of metabolism, or end stage renal disease; in some embodiments, the subject is in need of treatment for sepsis and is being treated and/or has been treated for a metabolic disorder, an inborn error of metabolism, or end stage renal disease.

In some embodiments, the subject has had an immune responses within a continuum from infection to multiple organ dysfunction syndrome. In some embodiments, the subject has systemic inflammatory response syndrome (SIRS), e.g., in some embodiments the subject has two or more of abnormal body temperature, heart rate, respiratory rate or blood gas, and white blood cell count. In some embodiments, the subject has SIRS in response to an infectious process, e.g., the subject has sepsis. In some embodiments, the subject has severe sepsis, e.g., the subject has sepsis and sepsis-induced organ dysfunction or tissue hypoperfusion (e.g., the subject has hypotension, elevated lactate, or decreased urine output). In some embodiments, the subject has severe sepsis, e.g., the subject has a natural immune response to an infection that triggers widespread inflammation and blood clotting in tiny vessels throughout the body. In some embodiments, the subject has failure of critical organs in the body. In some embodiments the subject has septic shock, e.g., the subject has severe sepsis and persistently low blood pressure.

Pharmaceutical Preparations and Dosages

It is generally contemplated that the carnitine treatments according to the technology are formulated for administration to a mammal, and especially to a human with a condition that is responsive to the administration of such compounds (e.g., sepsis). Therefore, where carnitine is administered in a pharmacological composition, it is contemplated that the carnitine is formulated in admixture with a pharmaceutically acceptable carrier. For example, carnitine can be administered orally as pharmacologically acceptable salts, or intravenously in a physiological saline solution (e.g., buffered to a pH of about 6.0 to 7.5). Conventional buffers such as phosphates, bicarbonates, or citrates can be used for this purpose. Of course, one of ordinary skill in the art may modify the formulations within the teachings of the specification to provide numerous formulations for a particular route of administration. In particular, contemplated compounds may be modified to render them more soluble in water or other vehicle, which for example, may be easily accomplished with minor modifications (salt formulation, esterification, etc.) that are well within the ordinary skill in the art. It is also well within the ordinary skill of the art to modify the route of administration and dosage regimen of a particular compound to manage the pharmacokinetics of the present compounds for maximum beneficial effect in a patient.

In certain pharmaceutical dosage forms, prodrug forms of carnitine may be formed for various purposes, including reduction of toxicity, increasing the organ or target cell specificity, etc. Among various prodrug forms, acylated (acetylated or other) derivatives, pyridine esters, and various salt forms of the present compounds are preferred. One of ordinary skill in the art will recognize how to readily modify the present compounds to prodrug forms to facilitate delivery of active compounds to a target site within the host organism or patient. One of ordinary skill in the art will also take advantage of favorable pharmacokinetic parameters of the prodrug forms, where applicable, in delivering the present compounds to a targeted site within the host organism or patient to maximize the intended effect of the compound. Similarly, it should be appreciated that a carnitine prodrug may also be metabolized to its biologically active form, and all metabolites of the compounds herein are therefore specifically contemplated. In addition, carnitine may be administered in combination with yet further agents.

With respect to administration to a subject, it is contemplated that the carnitine be administered in a pharmaceutically effective amount. One of ordinary skill recognizes that a pharmaceutically effective amount varies depending on the therapeutic agent used, the subject's age, condition, and sex, and on the extent of the disease in the subject. Generally, the dosage should not be so large as to cause adverse side effects, such as hyperviscosity syndromes, pulmonary edema, congestive heart failure, and the like. The dosage can also be adjusted by the individual physician or health care provider to achieve the desired therapeutic goal.

As used herein, the actual amount encompassed by the term "pharmaceutically effective amount" will depend on the route of administration, the type of subject being treated, and the physical characteristics of the specific subject under consideration. These factors and their relationship to determining this amount are well known to skilled practitioners in the medical, veterinary, and other related arts. This amount and the method of administration can be tailored to maximize efficacy but will depend on such factors as weight, diet, concurrent medication, and other factors that those skilled in the art will recognize.

Pharmaceutical compositions preferably comprise carnitine associated with one or more pharmaceutically acceptable carriers, diluents, or excipients. Pharmaceutically acceptable carriers are known in the art such as those described in, for example, *Remingtons Pharmaceutical Sciences*, Mack Publishing Co. (A. R. Gennaro edit. 1985), explicitly incorporated herein by reference for all purposes.

Accordingly, in some embodiments, the carnitine is formulated as a tablet, a capsule, a time release tablet, a time release capsule; a time release pellet; a slow release tablet, a slow release capsule; a slow release pellet; a fast release tablet, a fast release capsule; a fast release pellet; a sublingual tablet; a gel capsule; a microencapsulation; a transdermal delivery formulation; a transdermal gel; a transdermal patch; a sterile solution; a sterile solution prepared for use as an intramuscular or subcutaneous injection, for use as a direct injection into a targeted site, or for intravenous administration; a solution prepared for rectal administration; a solution prepared for administration through a gastric feeding tube or duodenal feeding tube; a suppository for rectal administration; a liquid for oral consumption prepared as a solution or an elixir; a topical cream; a gel; a lotion; a tincture; a syrup; an emulsion; or a suspension.

In some embodiments, the time release formulation is a sustained-release, sustained-action, extended-release, controlled-release, modified release, or continuous-release mechanism, e.g., the composition is formulated to dissolve quickly, slowly, or at any appropriate rate of release of the compound over time.

In some embodiments, the compositions are formulated so that the carnitine is embedded in a matrix of an insoluble substance (e.g., various acrylics, chitin) such that the dissolving carnitine finds its way out through the holes in the matrix, e.g., by diffusion. In some embodiments, the formulation is enclosed in a polymer-based tablet with a laser-drilled hole on one side and a porous membrane on the other side. Stomach acids push through the porous membrane, thereby pushing the drug out through the laser-drilled hole. In time, the entire drug dose releases into the system while the polymer container remains intact, to be excreted later through normal digestion. In some sustained-release formulations, the compound dissolves into the matrix and the matrix physically swells to form a gel, allowing the compound to exit through the gel's outer surface. In some embodiments, the formulations are in a micro-encapsulated form, e.g., which is used in some embodiments to produce a complex dissolution profile. For example, by coating the compound around an inert core and layering it with insoluble substances to form a microsphere, some embodiments provide more consistent and replicable dissolution rates in a convenient format that is combined in particular embodiments with other controlled (e.g., instant) release pharmaceutical ingredients, e.g., to provide a multipart gel capsule.

In some embodiments, the pharmaceutical preparations and/or formulations of the technology are provided in particles. "Particles" as used herein means nano- or microparticles (or in some instances larger) that can consist in whole or in part of the compounds as described herein. The particles may contain the preparations and/or formulations in a core surrounded by a coating, including, but not limited to, an enteric coating. The preparations and/or formulations also may be dispersed throughout the particles. The preparations and/or formulations also may be adsorbed into the particles. The particles may be of any order release kinetics, including zero order release, first order release, second order release, delayed release, sustained release, immediate release, and any combination thereof, etc. The particle may include, in addition to the preparations and/or formulations, any of those materials routinely used in the art of pharmacy and medicine, including, but not limited to, erodible, non-erodible, biodegradable, or nonbiodegradable materials or combinations thereof. The particles may be microcapsules which contain the formulation in a solution or in a semi-solid state. The particles may be of virtually any shape.

Both non-biodegradable and biodegradable polymeric materials can be used in the manufacture of particles for delivering the preparations and/or formulations. Such polymers may be natural or synthetic polymers. The polymer is selected based on the period of time over which release is desired. Bioadhesive polymers of particular interest include bioerodible hydrogels described by H. S. Sawhney, C. P. Pathak and J. A. Hubell in *Macromolecules*, (1993) 26: 581-587, the teachings of which are incorporated herein by reference. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly (isobutyl methacrylate), poly(hexylmethacrylate), poly(isodecyl methacrylate), poly(lauryl methacrylate), poly(phenylmethacrylate), poly(methyl acrylate), poly(isopropyl acrylate), poly(isobutyl acrylate), and poly(octadecyl acrylate).

The technology also provides methods for preparing stable pharmaceutical preparations containing aqueous solutions of carnitine or salts thereof to inhibit formation of degradation products. A solution is provided that contains carnitine or salts thereof and at least one inhibiting agent. The solution is processed under at least one sterilization technique prior to and/or after terminal filling the solution in the sealable container to form a stable pharmaceutical preparation. The present formulations may be prepared by various methods known in the art so long as the formulation is substantially homogenous, e.g., the pharmaceutical is distributed substantially uniformly within the formulation. Such uniform distribution facilitates control over drug release from the formulation.

In some embodiments, the carnitine is formulated with a buffering agent. The buffering agent may be any pharmaceutically acceptable buffering agent. Buffer systems include citrate buffers, acetate buffers, borate buffers, and phosphate buffers. Examples of buffers include citric acid, sodium citrate, sodium acetate, acetic acid, sodium phosphate and phosphoric acid, sodium ascorbate, tartartic acid, maleic acid, glycine, sodium lactate, lactic acid, ascorbic acid, imidazole, sodium bicarbonate and carbonic acid, sodium succinate and succinic acid, histidine, and sodium benzoate and benzoic acid.

In some embodiments, the carnitine is formulated with a chelating agent. The chelating agent may be any pharmaceutically acceptable chelating agent. Chelating agents include ethylenediaminetetraacetic acid (also synonymous with EDTA, edetic acid, versene acid, and sequestrene), and EDTA derivatives, such as dipotassium edetate, disodium edetate, edetate calcium disodium, sodium edetate, trisodium edetate, and potassium edetate. Other chelating agents include citric acid and derivatives thereof. Citric acid also is known as citric acid monohydrate. Derivatives of citric acid include anhydrous citric acid and trisodiumcitrate-dihydrate. Still other chelating agents include niacinamide and derivatives thereof and sodium desoxycholate and derivatives thereof.

In some embodiments, the carnitine is formulated with an antioxidant. The antioxidant may be any pharmaceutically acceptable antioxidant. Antioxidants are well known to those of ordinary skill in the art and include materials such as ascorbic acid, ascorbic acid derivatives (e.g., ascorbylpalmitate, ascorbylstearate, sodium ascorbate, calcium ascorbate, etc.), butylated hydroxy anisole, buylated hydroxy toluene, alkylgallate, sodium meta-bisulfate, sodium bisulfate, sodium dithionite, sodium thioglycollic acid, sodium formaldehyde sulfoxylate, tocopherol and derivatives thereof, (d-alpha tocopherol, d-alpha tocopherol acetate, dl-alpha tocopherol acetate, d-alpha tocopherol succinate, beta tocopherol, delta tocopherol, gamma tocopherol, and d-alpha tocopherol polyoxyethylene glycol 1000 succinate) monothioglycerol, and sodium sulfite. Such materials are typically added in ranges from 0.01 to 2.0%.

In some embodiments, the carnitine is formulated with a cryoprotectant. The cryoprotecting agent may be any pharmaceutically acceptable cryoprotecting agent.

Common cryoprotecting agents include histidine, polyethylene glycol, polyvinyl pyrrolidine, lactose, sucrose, mannitol, and polyols.

In some embodiments, the carnitine is formulated with an isotonicity agent. The isotonicity agent can be any pharmaceutically acceptable isotonicity agent. This term is used in the art interchangeably with iso-osmotic agent, and is known as a compound which is added to the pharmaceutical preparation to increase the osmotic pressure, e.g., in some embodiments to that of 0.9% sodium chloride solution, which is iso-osmotic with human extracellular fluids, such as plasma. Preferred isotonicity agents are sodium chloride, mannitol, sorbitol, lactose, dextrose and glycerol.

The pharmaceutical preparation may optionally comprise a preservative. Common preservatives include those selected from the group consisting of chlorobutanol, parabens, thimerosol, benzyl alcohol, and phenol. Suitable preservatives include but are not limited to: chlorobutanol (0.3-0.9% w/v), parabens (0.01-5.0%), thimerosal (0.004-0.2%), benzyl alcohol (0.5-5%), phenol (0.1-1.0%), and the like.

In some embodiments, the carnitine is formulated with a humectant to provide a pleasant mouth-feel in oral applications. Humectants known in the art include cholesterol, fatty acids, glycerin, lauric acid, magnesium stearate, pentaerythritol, and propylene glycol.

In some embodiments, an emulsifying agent is included in the formulations, for example, to ensure complete dissolution of all excipients, especially hydrophobic components such as benzyl alcohol. Many emulsifiers are known in the art, e.g., polysorbate 60.

For some embodiments related to oral administration, it may be desirable to add a pharmaceutically acceptable flavoring agent and/or sweetener. Compounds such as saccharin, glycerin, simple syrup, and sorbitol are useful as sweeteners.

Administration, Treatments, and Dosing

In some embodiments, the technology relates to methods of providing a dosage of carnitine to a subject. In some embodiments, carnitine, a derivative thereof, or a pharmaceutically acceptable salt thereof, is administered in a pharmaceutically effective amount. In some embodiments, carnitine, a derivative thereof, or a pharmaceutically acceptable salt thereof, is administered in a therapeutically effective dose.

The dosage amount and frequency are selected to create an effective level of the compound without substantially harmful effects. When administered orally or intravenously, the dosage of the compound or related compounds will generally range from 0.001 to 10,000 mg/kg/day or dose (e.g., 0.01 to 1000 mg/kg/day or dose; 0.1 to 100 mg/kg/day or dose).

Methods of administering a pharmaceutically effective amount include, without limitation, administration in parenteral, oral, intraperitoneal, intranasal, topical, sublingual, rectal, and vaginal forms. Parenteral routes of administration include, for example, subcutaneous, intravenous, intramuscular, intrastemal injection, and infusion routes. In some embodiments, the compound, a derivative thereof, or a pharmaceutically acceptable salt thereof, is administered orally.

In some embodiments, a single dose of a compound or a related compound is administered to a subject. In other embodiments, multiple doses are administered over two or more time points, separated by hours, days, weeks, etc. In some embodiments, compounds are administered over a long period of time (e.g., chronically), for example, for a period of months or years (e.g., 1, 2, 3, 4, 5, 6, 7, 8, 9, 10, 11, 12, or more months or years). In such embodiments, compounds may be taken on a regular scheduled basis (e.g., daily, weekly, etc.) for the duration of the extended period.

The technology also relates to methods of treating a subject with carnitine for the subject's malady (e.g., sepsis). According to another aspect of the technology, a method is provided for treating a subject in need of such treatment with an effective amount of carnitine or a salt thereof. The method involves administering to the subject an effective amount of carnitine or a salt thereof in any one of the pharmaceutical preparations described above, detailed herein, and/or set forth in the claims. The subject can be any subject in need of such treatment, e.g., for sepsis. In the foregoing description, the technology is in connection with carnitine or salts thereof. Such salts include, but are not limited to, bromide salts, chloride salts, iodide salts, carbonate salts, and sulfate salts. It should be understood, however, that the compound is a member of a class of compounds and the technology is intended to embrace pharmaceutical preparations, methods, and kits containing related derivatives within this class. Another aspect of the technology then embraces the foregoing summary but read in each aspect as if any such derivative is substituted wherever "carnitine" appears.

In some embodiments, a subject is tested to assess the presence, the absence, or the level of a malady such as sepsis. Such testing is performed, e.g., by assaying or measuring a detectable agent such as a biomarker or a metabolite as described herein, a physical symptom, an indication, etc., to determine the risk of or the presence of the malady or condition. In some embodiments, the subject is treated with carnitine based on the outcome of the test. In some embodiments, a subject is treated, a sample is obtained and the level of a detectable agent is measured, and then the subject is treated again based on the level of detectable agent that was measured. In some embodiments, a subject is treated, a sample is obtained and the level of detectable agent is measured, the subject is treated again based on the level of detectable agent that was measured, and then another sample is obtained and the level of detectable agent is measured. In some embodiments, other tests (e.g., not based on measuring the level of detectable agent) are also used at various stages, e.g., before the initial treatment as a guide for the initial dose. In some embodiments, a subsequent treatment is adjusted based on a test result, e.g., the dosage amount, dosage schedule, identity of the drug, etc. is changed. In some embodiments, a patient is tested, treated, and then tested again to monitor the response to therapy and/or change the therapy. In some embodiments, cycles of testing and treatment may occur without limitation to the pattern of testing and treating, the periodicity, or the duration of the interval between each testing and treatment phase. As such, the technology contemplates various combinations of testing and treating without limitation, e.g., test/treat, treat/test, test/treat/test, treat/test/treat, test/treat/test/treat, test/treat/test/treat/test, test/treat/test/test/treat/treat/test, treat/treat/test/treat, test/treat/treat/test/treat/treat, etc.

Exemplary Carnitine Formulations and Dosages

In some specific embodiments, carnitine is provided as an injectable solution comprising 1 g of L-carnitine in a 5 ml volume. Carnitine is readily soluble in water and hot alcohol, but is insoluble in acetone. In some embodiments the pH is adjusted to 6.0 to 6.5, e.g., with hydrochloric acid or sodium hydroxide. In some embodiments, carnitine is mixed in parenteral solutions of sodium chloride 0.9% or Lactated Ringer's in concentrations ranging from 250 mg/500 mL (0.5 mg/mL) to 4200 mg/500 mL (8.0 mg/mL) and stored at room temperature (25° C.) for up to 24 hours in PVC plastic bags.

In some embodiments, carnitine is provided as an oral formulation, e.g., in a tablet or solution. Bioavailability studies indicated that carnitine provided in tablet form was bio-equivalent to carnitine provided in oral solution. For example, 4 days of dosing with 6×330-mg tablets of carnitine twice a day or 2 g of carnitine oral solution twice a day, the maximum plasma concentration ($C_{max}$) was about 80 µmol/liter and the time to maximum plasma concentration ($T_{max}$) occurred at 3.3 hours.

In some embodiments, L-carnitine is administered by infusion, e.g., over 1 to 24 hours, e.g., for approximately 12 hours. In some embodiments, L-carnitine is administered intravenously by syringe as a 4-g bolus injection (in, e.g., 20 mL) over 2 to 3 minutes followed by an 8-g infusion (8 g in 1000 mL of 0.9% normal saline or approximately 8 mg/mL) over the following 12 hours (83 ml/hour).

In some embodiments, dosages are from 1 to 100 mg/kg (e.g., 1, 5, 10, 20, 30, 40, 50, 60, 70, 80, 90, or 100 mg/kg). In some embodiments, dosages are higher than 100 mg/kg, e.g., 200, 300, 400, or 500 mg/kg.

Previous studies have indicated that the recommended dosage for metabolic disorders is 50 mg/kg given as a slow 2 to 3 minute bolus injection or by infusion. In some embodiments, a loading dose is given in patients with severe metabolic crisis, followed by an equivalent dose over the following 24 hours. It should be administered every three or four hours, and usually not less than every 6 hours either by infusion or by intravenous injection. In some embodiments, subsequent daily doses are in the range of 50 mg/kg or as therapy may require. In studies of safety and efficacy, the highest dose administered has been 300 mg/kg.

In some embodiments, carnitine is provided as levocarnitine (CARNITOR®, sigma-tau Pharmaceuticals, Inc.)

Methods

The technology relates to methods for treating a subject (e.g., a subject having sepsis or a metabolic deficiency) with carnitine, methods for predicting a subject's response to treatment with carnitine, and methods for monitoring treatment of a subject with carnitine. In some embodiments, biomarkers (e.g., blood serum metabolites) measured prior to carnitine treatment are predictive of the level of carnitine that will be attained in the subject's blood after treatment with carnitine. Accordingly, biomarkers (e.g., blood serum metabolites) measured prior to carnitine treatment are used to identify subjects for whom treatment with carnitine is likely to be successful. Particular biomarkers that are encompassed by the technology are ketone bodies such as acetoacetate and 3-hydroxybutyrate. As indicated by experimental data collected during the development of the technology described, a subject having a concentration of serum acetoacetate less than or equal to approximately 25 µM or a concentration of 3-hydroxybutyrate less than or equal to approximately 150 µM prior to treatment with carnitine is expected to have a lower carnitine concentration or an acetylcarnitine concentration at 24 hours after the administration of carnitine and a lower mortality when compared with a subject with higher pre-treatment ketone bodies levels that is treated with carnitine. In some embodiments the subject has sepsis and the carnitine administration remedies a metabolic abnormality associated with sepsis.

In some embodiments, a combination of biomarkers is measured, e.g., a level of a ketone body and one or more of procalcitonin (PCT), C-reactive protein (CRP), and/or heparin binding protein (HBP). PCT is the pro-hormone of calcitonin and is commonly used to differentiate a bacterial infection immune response from a viral infection or an inflammatory response not linked to a pathogen. CRP is a marker of inflammation. HBP originates from neutrophils when exposed to bacteria in the blood stream. The blood level of HBP is used to identify patients likely to develop sepsis. An elevated level of one or more of these biomarkers is indicative of sepsis and an elevated level of a ketone body indicates that carnitine treatment is less likely to be a successful treatment for sepsis.

In some embodiments, a biomarker is assayed, evaluated, or measured in combination with detecting a symptom associated with sepsis such as abnormal body temperature, heart rate, respiratory rate, blood gas, or white blood cell count; hypotension; elevated lactate; decreased urine output; inflammation; blood clotting; or persistently low blood pressure.

In some embodiments, treatment comprises administering carnitine in combination with one or more other therapeutic agents. For example, in some embodiments carnitine is administered in a treatment regimen that also includes administering activated protein C. In some embodiments, carnitine and activated protein C are administered simultaneously and in some embodiments carnitine and activated protein C are administered sequentially (e.g., carnitine is administered after or before the activated protein C). In some embodiments carnitine is administered in a treatment regimen that also includes administering an antibiotic. In some embodiments, carnitine and an antibiotic are administered simultaneously and in some embodiments carnitine and an antibiotic are administered sequentially (e.g., carnitine is administered after or before the antibiotic).

After treatment with carnitine, the technology provides biomarkers that are associated with metabolic changes produced by carnitine treatment. Data collected during the development of the technology indicated that the levels of carnitine and 0-acetyl-carnitine increased after administration of carnitine (e.g., 24 hours after administration of carnitine). In addition, the levels of certain amino acids (e.g., methionine, lysine, phenylalanine, tyrosine, ornithine, serine, threonine, valine) are associated with the metabolic response to carnitine treatment. These amino acids thus provide a biomarker useful to monitor treatment and adjust dosages of carnitine. As indicated by the data collected, these amino acids (in particular, phenylalanine, tyrosine, ornithine, serine, threonine, and valine) increased 24 to 48 hours after carnitine treatment. In addition, the level of citrate increased after carnitine treatment, indicating that the carnitine was associated with adjusting a metabolic abnormality in the subject.

In some embodiments, changes in metabolite biomarkers are associated with monitoring and ameliorating adverse reactions to treatment with carnitine. For instance, the technology provides for monitoring treatment of sepsis in subjects with a metabolic disorder associated with one of the metabolites affected by treatment with carnitine to reduce or eliminate adverse responses to carnitine treatment. As a particular example, a subject having phenylketonuria (PKU) may be sensitive to increases in phenylalanine caused by carnitine treatment and thus the treatment could be monitored and adjusted accordingly to accommodate the subject's intolerance of phenylalanine.

Data Analysis

In some embodiments, a computer-based analysis program is used to translate the biomarker data generated by a detection assay (e.g., the level of one or more biomarkers, e.g., as determined by using one or more detection reagents) into data of predictive value for a clinician. The clinician can access the predictive data using any suitable means. Thus, in some preferred embodiments, the present technology provides the further benefit that the clinician, who is not likely to be trained in genetics or molecular biology, need not understand the raw data. The data are presented directly to the clinician in its most useful form. The clinician is then able to utilize the information in order to optimize the care of the subject.

The present technology contemplates any method capable of receiving, processing, and transmitting the information to and from laboratories conducting the assays, information providers, medical personnel, and subjects. For example, in some embodiments of the present technology, a sample (e.g., blood, serum, plasma, etc.) is obtained from a subject and submitted to a profiling service (e.g., clinical lab at a medical facility, genomic profiling business, etc.) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication system). Once received by the profiling service, the sample is processed and a profile or report is produced that is specific for the diagnostic or prognostic information desired for the subject.

The profile data is then prepared in a format suitable for interpretation by a treating clinician. For example, rather than providing raw biomarker levels, the prepared format may represent a diagnosis or risk assessment (e.g., prognosis of sepsis or sepsis-related problems) for the subject, along with recommendations for particular treatment options (e.g., whether to administer carnitine and/or a carnitine dosage to administer). The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The biomarker data is then sent to a central processing facility for further analysis and/or to convert the biomarker data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subjects or medical personnel are able to access the data and/or report using the electronic communication system. The subject may chose further intervention or counseling based on the results. In some embodiments, the data is used for research use. For example, the data may be used to further optimize the inclusion or elimination of biomarkers as useful indicators of a particular condition or stage of disease or as a companion diagnostic to determine a treatment course of action.

EXAMPLES

Example 1—Metabolomics of Sepsis Patients Treated with Carnitine

L-carnitine (LC) has therapeutic potential based on its ability to remedy sepsis-induced metabolic dysfunction. Pharmacometabolomics allows for the systematic evaluation of the metabolic response to treatment. Accordingly, during the development of embodiments of the technology provided herein, experiments were conducted to collect metabolic profile data as a function of treatment with LC and to determine if sub-groups of patients exhibit differential responses to LC treatment.

Serum samples were collected from patients enrolled in a previously published double-blind randomized phase I clinical trial of L-carnitine treatment for sepsis (see, e.g., Puskarich et al., J Parenter Enteral Nutr 38(6): 736-743, incorporated herein by reference in its entirety). From this study, serum samples collected from carnitine-treated (n=16) and placebo-treated (n=15) patients were assayed by $^1$H-nuclear magnetic resonance (NMR) and the resulting spectra were used to identify and quantify metabolites; a total of 38 metabolites were identified in each sample.

Serum was assayed prior to (T0) and following (T24, T48) treatment with a single 12-g dose of LC or placebo. The T0 (pre-treatment) median 3-hydroxybutyrate and acetoacetate concentrations; and ratio of acetylcarnitine to carnitine were different in patients categorized as "high" or "low" ketone but other clinical markers such as SOFA score and concentrations of lactate and glucose were not different across these groups (FIG. 1A-F). The data indicate that the sepsis patients can be differentiated into two groups based on the assayed ketone levels prior to administration of L-carnitine (see FIG. 1E and FIG. 1F). These two groups are the "high" ketone group (FIG. 1E and FIG. 1F, black and diagonal hatched bars) and the "low" ketone group (FIG. 1E and FIG. 1F, white and grey stippled bars). In particular, the "high" ketone groups had a pre-treatment serum acetoacetate level greater than approximately 50 µM and/or a pre-treatment serum 3-hydroxybutyrate level of greater than approximately 400 M; the "low" ketone groups had a pre-treatment serum acetoacetate level of less than or equal to approximately 25 µM and/or a concentration of 3-hydroxybutyrate less than or equal to approximately 150 µM (FIG. 1E and FIG. 1F). In addition, the data indicated that pre-treatment creatine was also higher in "high" ketone patients that were randomized to carnitine compared with the other groups.

Figure 2:
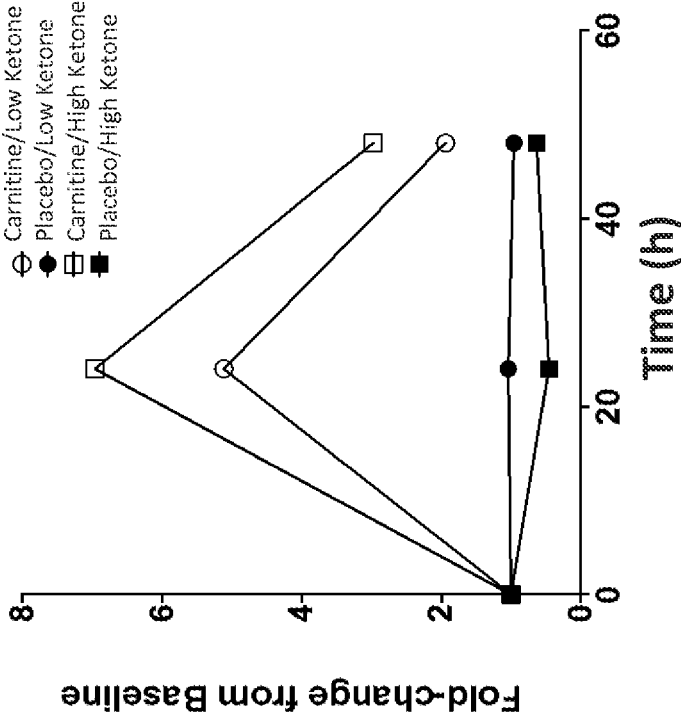
FIG. 2 is a series of plots showing the fold-changes in serum metabolites from pre-treatment (baseline) over the 48-hour study period: (A) carnitine and (B) O-acetyl-carnitine increased to a greater extent in "high" ketone carnitine-treated patients compared with "low" ketone carnitine-treated patients; (C) lysine and (D) methionine, precursors of carnitine, trended towards being higher in "low" ketone versus "high" ketone patients; and (E) phenylalanine and (F) tyrosine declined to a greater extent in placebo-treated "high" ketone patients. By 48 hours, amino acids (G) ornithine, (H) valine, (I) threonine, and (J) serine, were higher in "low" ketone compared with "high" ketone sepsis patients.
Figure 2:
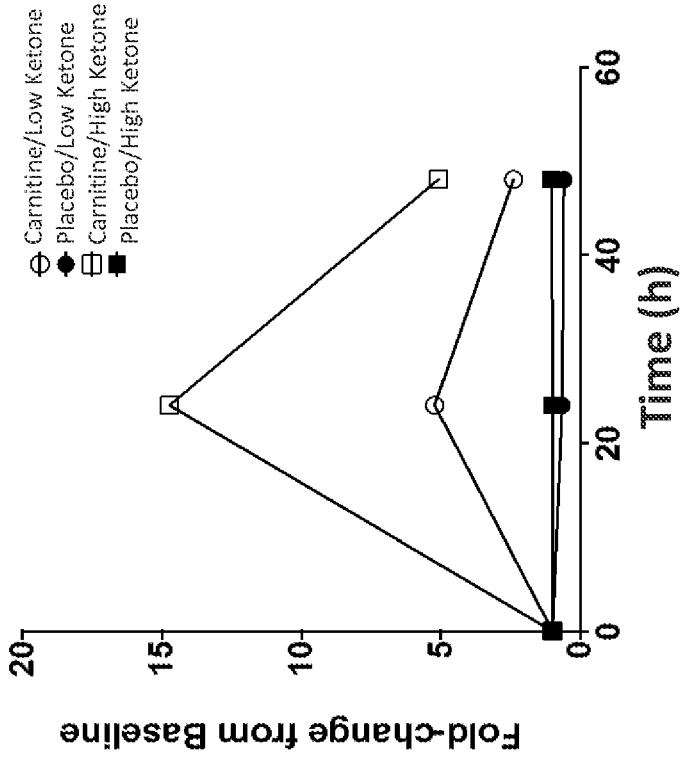
Figure 2:
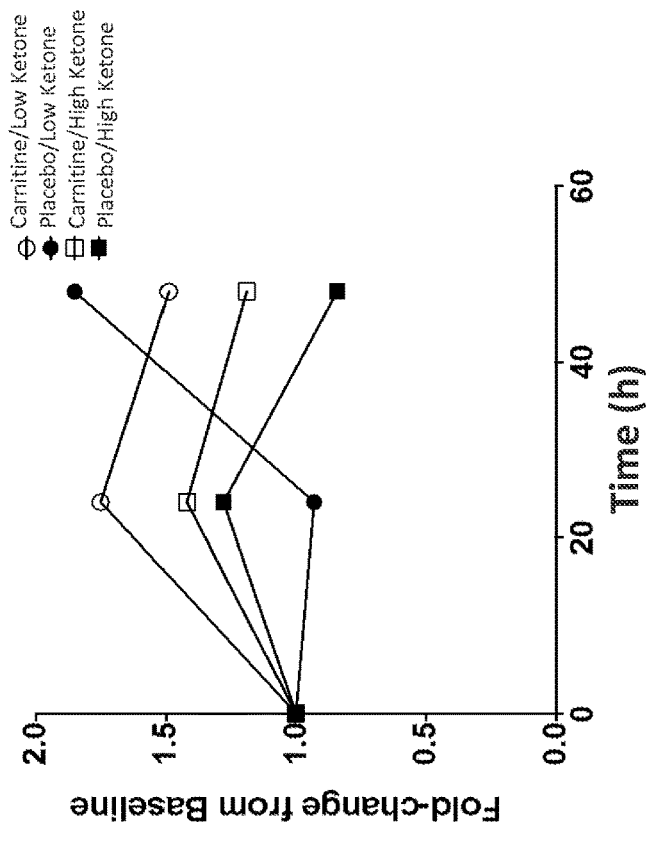
Figure 2:
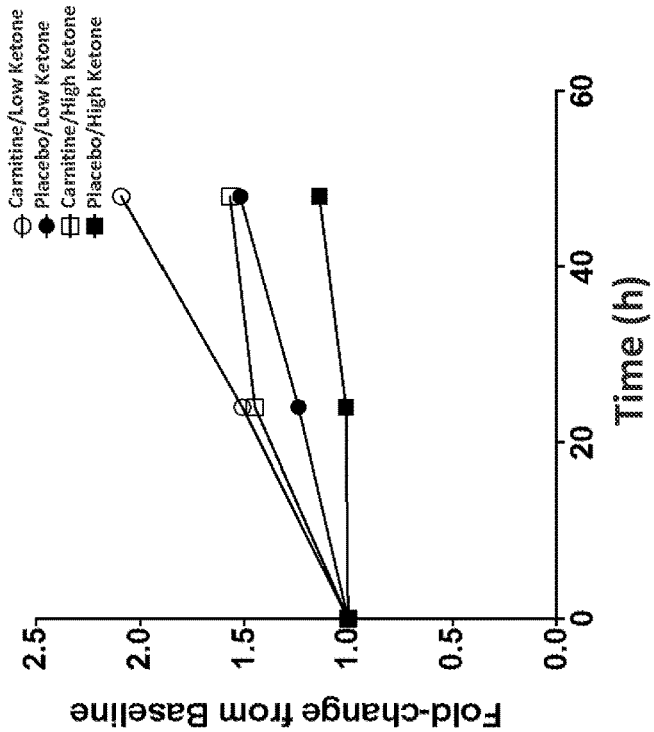
Figure 2:
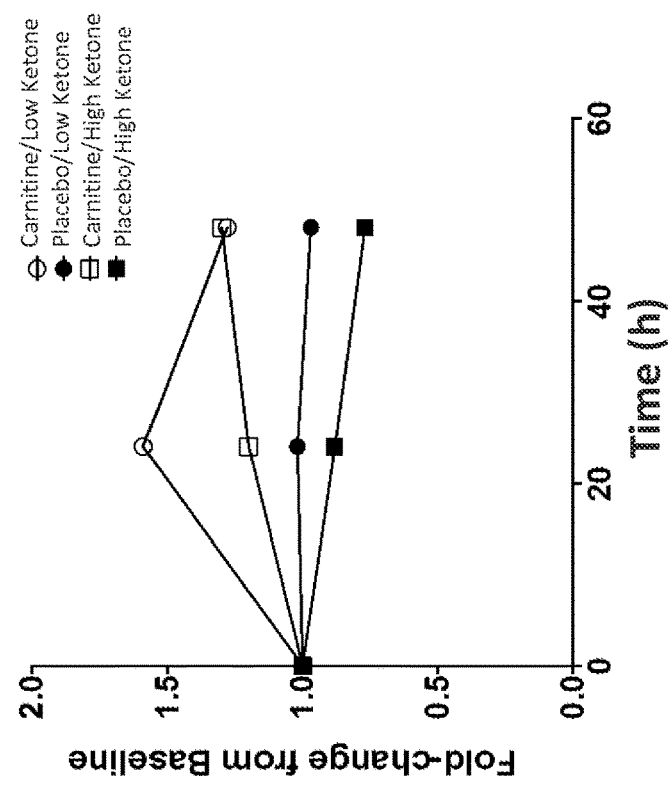
Figure 2:
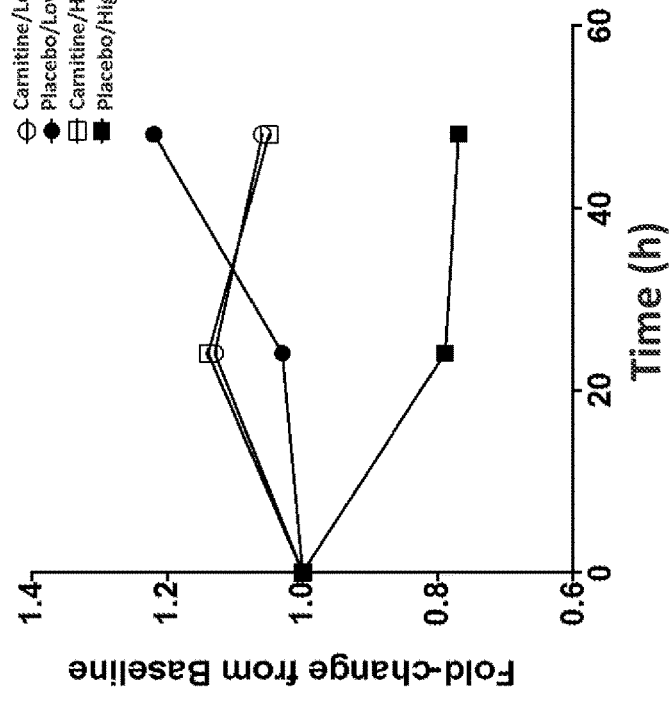
Figure 2:
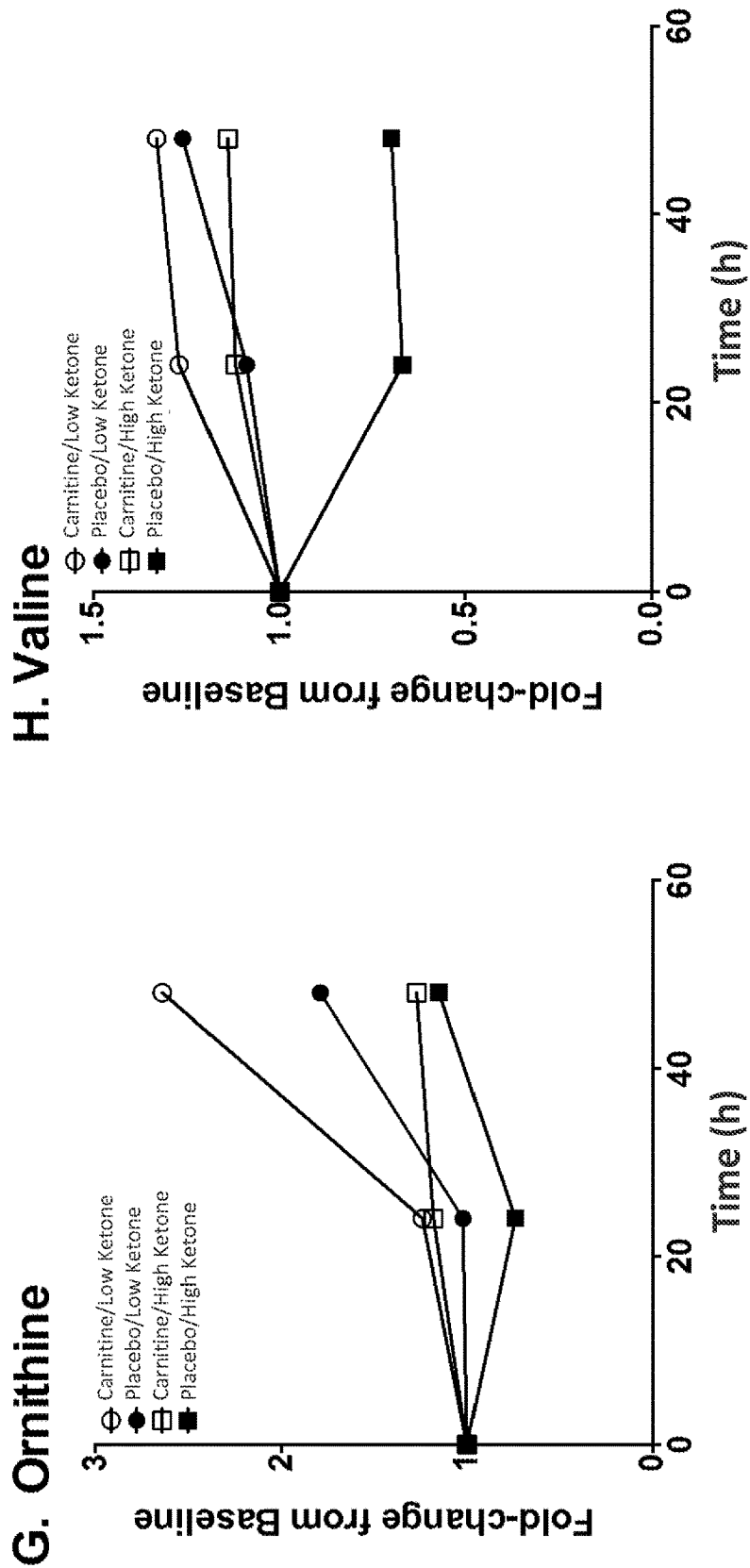
Figure 2:
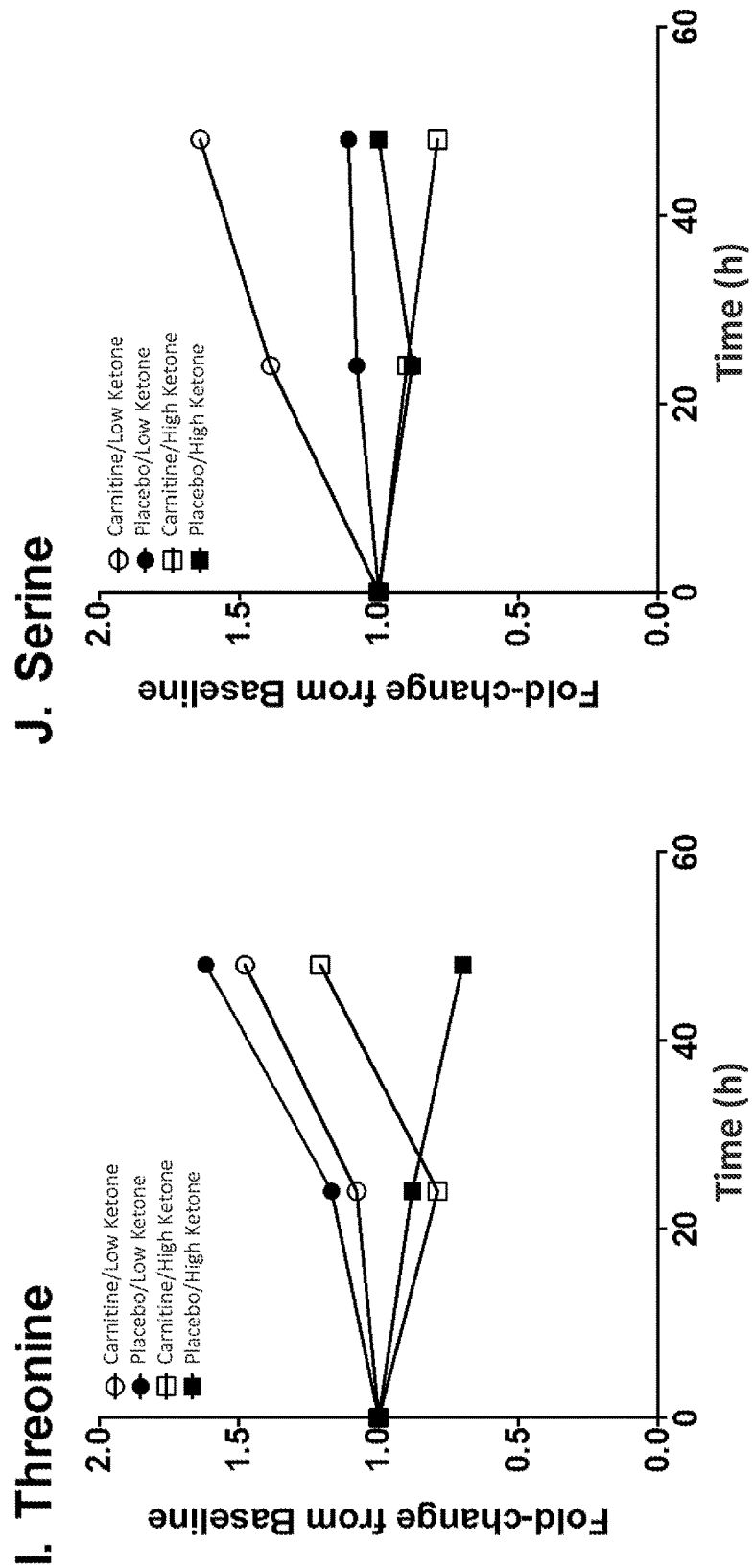

The levels of these metabolites were also measured in samples acquired at 24 hours and 48 hours after treatment with L-carnitine. The measured levels were used to calculate the relative changes (e.g., "fold-changes") in serum metabolites from the pre-treatment levels (baseline, T0) over the 48-hour study period. Carnitine (FIG. 2A) and O-acetylcarnitine (FIG. 2B) increased to a greater extent in "high" ketone carnitine-treated patients compared with "low" ketone carnitine-treated patients. Lysine (FIG. 2C) and methionine (FIG. 2D), precursors of carnitine, trended towards being higher in "low" ketone versus "high" ketone patients. Phenylalanine (FIG. 2E) and tyrosine (FIG. 2F), precursors of catecholamines, declined to a greater extent in placebo-treated "high" ketone patients. By 48 hours, the amino acids ornithine (FIG. 2G), valine (FIG. 2H), threonine (FIG. 2I), and serine (FIG. 2J) were higher in "low" ketone compared with "high" ketone sepsis patients. Another metabolite that shifted in response to LC treatment was citrate. Following a profound decline, citrate levels increased in LC-treated patients, suggesting an LC-mediated "salvage" of the sepsis-induced perturbation of the TCA cycle.

Figure 3:
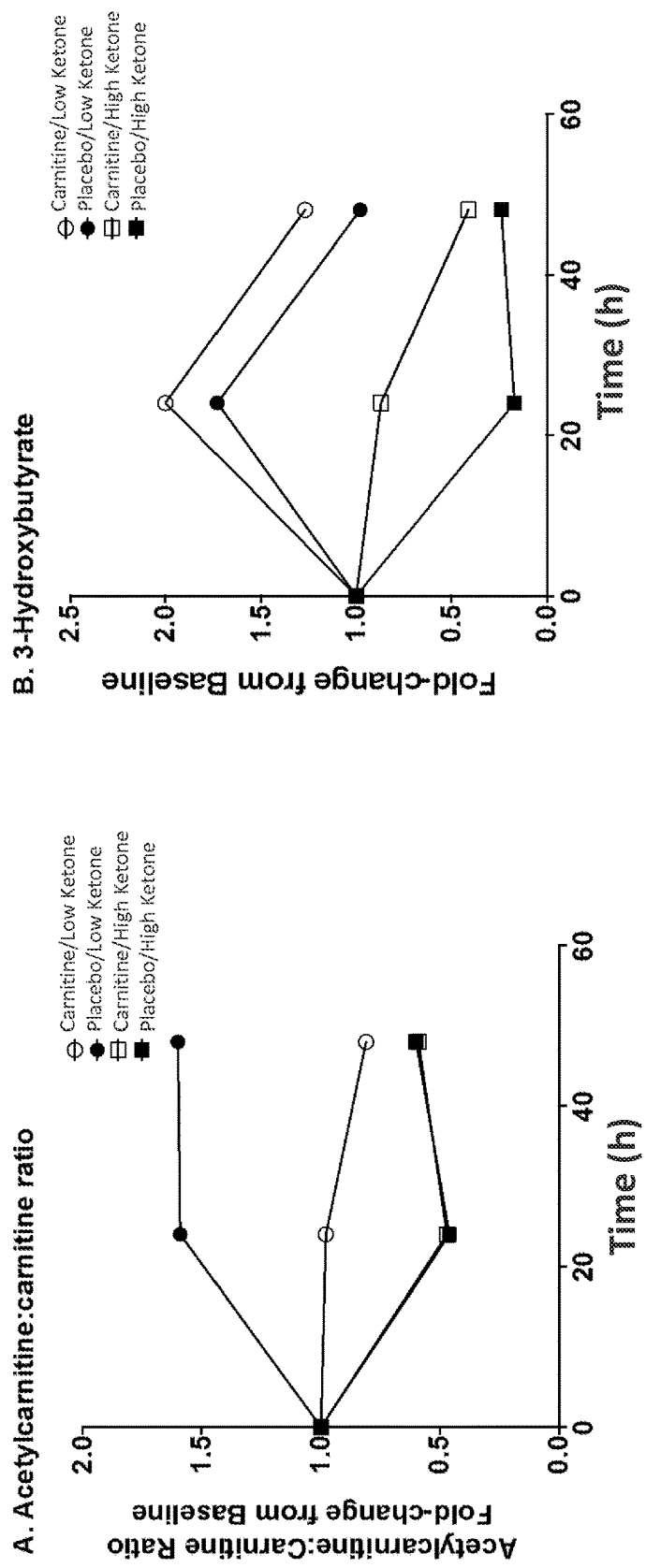
FIG. 3 is a series of plots showing the fold-changes in the serum (A) acetylcarnitine:carnitine (AC:C) ratio; (B) 3-hydroxybutyrate level; (C) acetoacetate level; and (D) glucose level. The AC:C ratio remained stable in the "low" ketone carnitine treated patients as did glucose, while ketone bodies increased over time.
Figure 3:
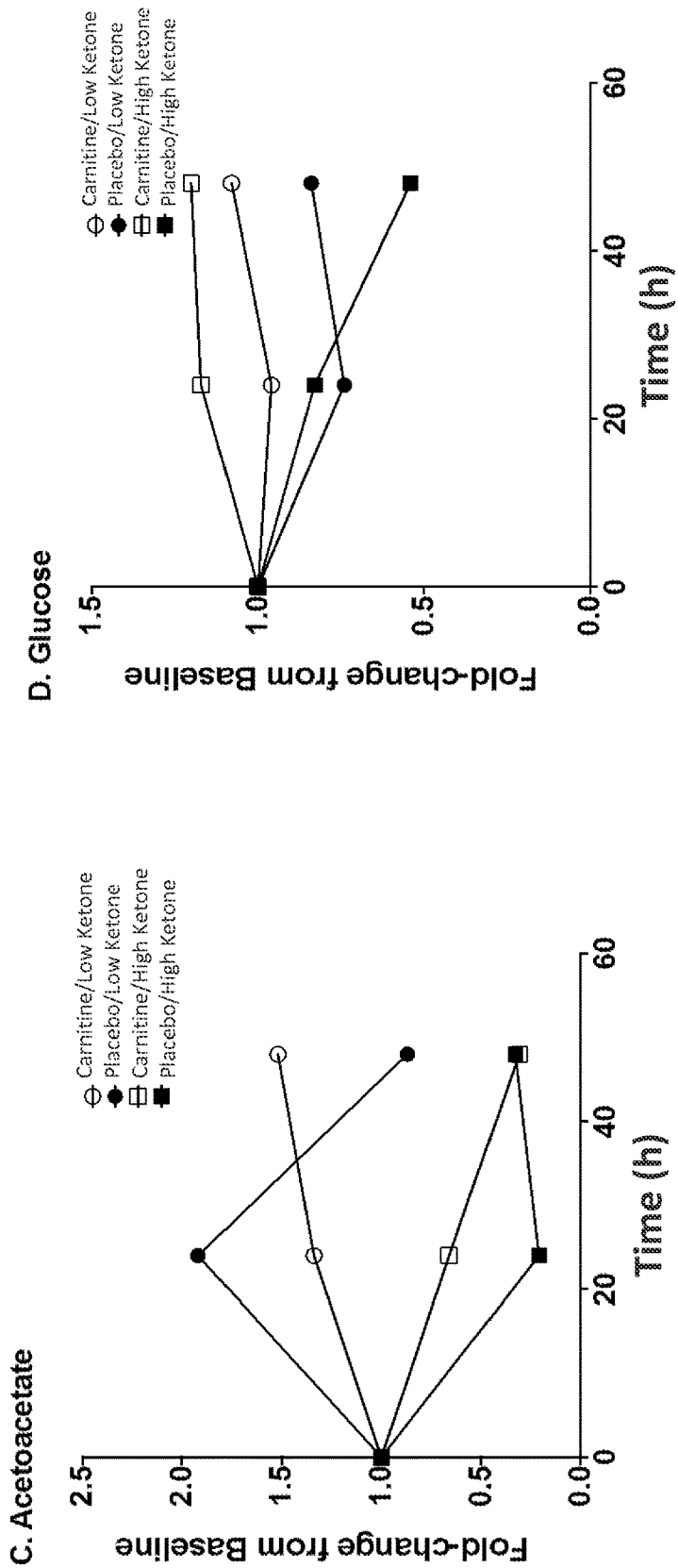
Figure 4:
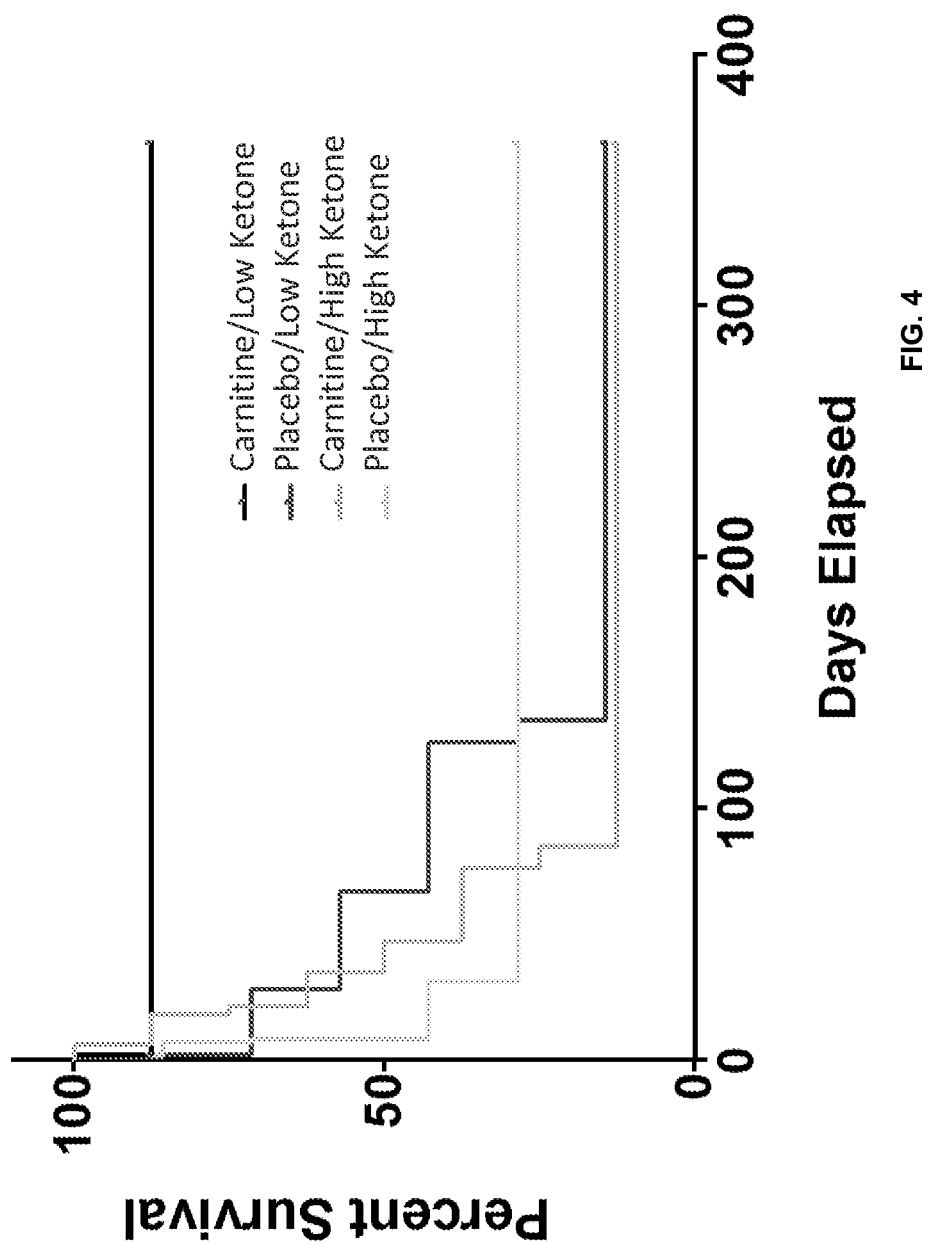
FIG. 4 shows the survival curves of the four groups in which carnitine-treated "low" ketone patients had dramatically improved survival compared with "low" ketone placebo treated patients and "high" ketone patients regardless of treatment.

Further, relative changes (e.g., "fold-changes") in the serum acetylcarnitine:carnitine (AC:C) ratio (FIG. 3A), serum 3-hydroxybutyrate (FIG. 3B), serum acetoacetate (FIG. 3C), and serum glucose (FIG. 3D) were measured and assessed relative to the pre-treatment levels (baseline, T0) over the 48-hour study period. The AC:C ratio remained stable in the "low" ketone carnitine treated patients as did glucose, while ketone bodies increased over time (see FIG. 3). Additional data indicated that carnitine-treated "low" ketone patients had dramatically improved survival (e.g., improved rate of survival at 1 year post-treatment) compared with "low" ketone placebo treated patients and "high" ketone patients regardless of treatment (FIG. 4).

These data indicate that LC administration produced a measureable change in the metabolome. In particular, changes in metabolite levels were detected for metabolites primarily related to the carnitine pathway and these data indicate that LC treatment of sepsis favorably influences sepsis-induced disruption of amino acid and energy metabolism.

Also, data collected indicate that pharmacometabolomics is useful to identify L-carnitine responsive phenotypes. Specifically, the data indicate that the pre-treatment metabolome of patients (e.g., in patients with sepsis) predicts the response of patients to treatment with LC—patients that have a pre-treatment acetoacetate concentration of less than or equal to approximately 25 μM or a 3-hydroxybutyrate concentration of less than or equal to approximately 150 μM are expected to attain lower levels of carnitine in the blood after treatment with carnitine compared with patients with elevated levels of acetoacetate or 3-hydroxybutyrate. This latter group of "high" ketone sepsis patients when treated with LC have higher carnitine levels at 24 hours and a higher mortality rate compared with the former group of "low" ketone patients.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A method for treating a subject having sepsis, the method comprising:
   a) measuring a level of acetoacetate or a level of 3-hydroxybutyrate in a sample from the subject;
   b) identifying the subject as a carnitine responsive subject if the acetoacetate level is less than or equal to 25 μM or the 3-hydroxybutyrate level is less than or equal to 150 μM; and
   c) administering carnitine to a carnitine responsive subject.

2. The method of claim 1 wherein the carnitine is administered intravenously.

3. The method of claim 2 wherein 1 g to 20 g of the carnitine is administered over 1 to 24 hours.

4. The method of claim 1 wherein the carnitine is administered orally.

5. The method of claim 4 wherein carnitine is provided in a dose of approximately 1 g to 3 g per dose.

6. The method of claim 1 wherein the administration of carnitine ameliorates a metabolic abnormality in the subject.

7. The method of claim 1 further comprising monitoring a concentration of one or more biomarkers selected from the group consisting of carnitine, 0-acetyl-carnitine, methionine, lysine, phenylalanine, tyrosine, ornithine, serine, threonine, valine, acetoacetate, 3-hydroxybutyrate, and citrate in a subject sample at a time that is from 20 to 100 hours after the administration of carnitine.

8. The method of claim 7 comprising identifying the subject as responding to carnitine treatment if an increase in the concentration of the one or more biomarkers is detected in the sample.

\* \* \* \* \*

UNITED STATES PATENT AND TRADEMARK OFFICE
CERTIFICATE OF CORRECTION

Page 1 of 1

PATENT NO. : 10,330,685 B2
APPLICATION NO. : 15/307920
DATED : June 25, 2019
INVENTOR(S) : Kathleen Stringer, Alan E. Jones and Mike Puskarich It is certified that error appears in the above-identified patent and that said Letters Patent is hereby corrected as shown below:

In the Claims

Claim 7, Column 22, Line 24 reads:
"group consisting of carnitine, 0-acetyl-carnitine, methio-"

Whereas it should read:
"group consisting of carnitine, O-acetyl-carnitine, methio-"

Signed and Sealed this
Twenty-fourth Day of December, 2019

Andrei Iancu
*Director of the United States Patent and Trademark Office*